United States Patent [19]

Schack et al.

[11] 4,222,968
[45] Sep. 16, 1980

[54] METHOD FOR SYNTHESIZING FLUOROCARBON HALIDES

[75] Inventors: Carl J. Schack, Chatsworth; Karl O. Christe, Calabasas, both of Calif.

[73] Assignee: United States of America as represented by the Secretary of the Air Force, Washington, D.C.

[21] Appl. No.: 46,898

[22] Filed: Jun. 8, 1979

[51] Int. Cl.$^2$ .............................................. C07C 19/08
[52] U.S. Cl. .................................................. 260/653
[58] Field of Search ............................. 260/653, 653.3

[56] References Cited

U.S. PATENT DOCUMENTS

| | | | |
|---|---|---|---|
| 2,176,181 | 10/1939 | Hunsdieker et al. | 260/487 |
| 3,072,730 | 1/1963 | Twelves | 260/653.7 |
| 3,555,100 | 1/1971 | Garth et al. | 260/653 |
| 3,822,323 | 7/1974 | Leverkusen et al. | 260/653 |
| 4,087,475 | 5/1978 | Jordan | 260/653 |
| 4,098,806 | 7/1978 | Commeyras et al. | 260/405.5 |

*Primary Examiner*—C. Davis
*Attorney, Agent or Firm*—Joseph E. Rusz; William J. O'Brien

[57] ABSTRACT

A method for synthesizing fluorocarbon halides by effecting a reaction at ambient temperatures between a fluorocarbon acid or its derivative and a halogen fluorosulfate.

5 Claims, No Drawings

METHOD FOR SYNTHESIZING FLUOROCARBON HALIDES

STATEMENT OF GOVERNMENT INTEREST

The invention and products described herein may be manufactured and used by or for the Government for governmental purposes without the payment of any royalty thereon.

BACKGROUND OF THE INVENTION

This invention relates to a process for synthesizing fluorocarbon halides. In a more particular manner, this invention concerns itself with a novel route for effecting the synthesis of fluorocarbon halides using halogen fluorosulfates as a reaction component.

Perfluorohalides are well known for their utility as intermediate precursors for a wide variety of synthetic reactions. At the present time there is no simple and convenient process for producing these compounds. One of the better known processes is that referred to as the Hunsdiecker reaction which is disclosed in M. Hudlicky, Chemistry of Organic Fluorine Compounds, 2nd Ed., Halsted Press, 225 (1976). In this reaction, the preparation of perfluorocarbon halides from fluorocarbon acids or their derivatives via decarboxylation requires the formation of the silver salt of the fluorocarbon acid. Since silver is required, the process is expensive. Also, the silver salt must then be vigorously dried prior to a reaction with an elemental halogen, such as chlorine, bromine or iodine, at elevated temperatures. The Hunsdiecker reaction is illustrated by the following equation.

$$R_fCO_2Ag + X_2 \rightarrow R_fX + AgX + CO_2 \quad (1)$$

wherein $R_f$ is a perfluoroalkyl radical and X is chlorine, bromine or iodine.

With the present invention, however, a novel, inexpensive, simple and efficient method has been found which utilizes halogen fluorosulfate having the general formula $$XSO_3F \quad (2)$$

wherein X is chlorine, bromine or iodine. The method of this invention eliminates the need for heating. Also, it permits the use of both the inexpensive fluorocarbon acids and their inexpensive alkali metal salts as a co-reactant, thus avoiding the requirement for the costly silver salts. The reaction between the fluorosulfate and the fluorocarbon acid takes place at ambient temperatures with a reaction temperature of from about 0° C. to 50° C. being preferred.

SUMMARY OF THE INVENTION

According to this invention a novel route to the synthesis of perfluorocarbon halides has been found that uses inexpensive reaction components. A suitable perfluorocarbon acid, or one of its derivatives, is reacted at ambient temperature with a halogen fluorosulfate in accordance with the following equation:

$$R_fCO_2M + XSO_3F \rightarrow R_fX + MSO_3F + CO_2 \quad (3)$$

wherein $R_f$ is a perfluoroalkyl radical, M is an alkali metal or hydrogen, and X is chlorine, bromine or iodine. The reaction takes place at a temperature within the preferred range of about 0° C. to 50° C.

Accordingly, the primary object of this invention is to provide a simple, efficient and inexpensive process for producing perfluorocarbon halides.

Another object of this invention is to provide a process for preparing perfluorocarbon halides that utilizes halogen fluorosulfates and the inexpensive perfluorocarbon acids, or their derivatives, as reaction components.

The above and still other objects and advantages of the present invention will become more readily apparent upon examination of the following detailed description thereof.

DESCRIPTION OF THE PREFERRED EMBODIMENT

With the above-described objects and advantages in mind, the present invention contemplates a novel process for synthesizing perfluorocarbon halides which find utility as precursors and intermediates in a variety of synthetic chemical reactions. Unfortunately, present processes involve decarboxylation and the use of expensive silver salts. This minimizes the ultimate use of perfluorocarbon halides because of the high costs involved in their preparation.

With this invention, however, a novel route to synthesizing these useful perfluorocarbon halides has been found. This new method utilizes halogen fluorosulfates and eliminates the need for heating. Also, it has the advantage that both the inexpensive fluorocarbon acids and their inexpensive alkali metal salts are utilized, thus eliminating the expensive silver salts as a reaction component. The process is best illustrated by the following reaction $$R_fCO_2M + XSO_3F \rightarrow R_fX + MSO_3F + CO_2 \quad (4)$$

wherein $R_f$ is a saturated, straight or branched chain perfluoroalkyl radical containing from one to ten carbon atoms, M is selected from the alkali metals or hydrogen, and X is chlorine, bromine or iodine. The reaction is conducted at ambient temperatures at the preferred range of about 0° C. to 50° C.

The tables which follow further illustrate the invention and provide typical results for reactions involving chlorine fluorosulfate as one component and a perfluoroalkyl acid, or its alkali metal salt derivative, as the other reaction component. Table I discloses perfluoroalkyl acid salts reacting with chlorine fluorosulfate while Table II discloses the reaction with perfluoroalkyl acids.

TABLE I

| Reactant | Product (%) |
|---|---|
| $ClCF_2CO_2Na$ | $CF_2Cl_2(28), ClCF_2SO_3F(39)$ |
| $CF_3CF_2CO_2Na$ | $CF_3CF_2Cl(79)$, some $CF_3CF_2SO_3F, CF_3Cl$ |
| $C_7F_{15}CO_2Na$ | $C_7F_{15}Cl(78), C_6F_{13}CFO(18)$ |

TABLE II

| Reactant | Product (%) |
|---|---|
| $CF_3CO_2H$ | $CF_3Cl(90)$, some $COF_2$ |
| $ClCF_2CO_2H$ | $CF_2Cl_2(85)$, some $ClCF_2SO_3F$ |
| $CF_2(CF_2CO_2H)_2$ | $CF_2(CF_2Cl)_2(86), ClCF_2CF_2CFO(11)ClCF_2CF_2CF_2SO_3F(1)$ |

Prior to this invention, no convenient method existed for shortening the fluorocarbon chains in fluorocarbons containing terminal —$CF_2Hal$ groups. Furthermore, in the typical Hunsdiecker reaction referred to heretofore, the chain could be shortened only by one carbon unit, because the resulting $CF_2Hal$ terminal group was resistant to further attack. This drawback is overcome by the present invention and repetitive chain shortenings can now be carried out.

A combination of the present invention with the previously known steps (ref. 1-3) of converting a —$CF_2Hal$ group into a —$CO_2M$ group can then be used to achieve a novel high yield chain shortening process, as demonstrated by the following equations:

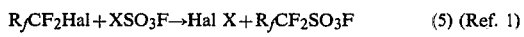  (5) (Ref. 1)

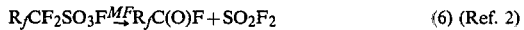  (6) (Ref. 2)

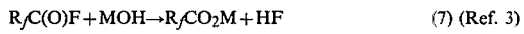  (7) (Ref. 3)

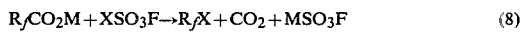  (8)

References
1. D. DesMarteau, Inorg. Chem.,7, 434 (1968).
2. M. Lustig and J. K, Ruff, Inorg. Chem.,3, 287 (1964).
3. ACS Monograph Series No. 138, "Aliphatic Fluorine Compounds", Reinhold, N.Y. (1958) p. 202

Since the product from this chain shortening process if a suitable starting material for repeating this cycle, this chain shortening can be carried out over and over, thus allowing any number of shortening steps.

The reaction of equation 8 is illustrated in the Examples which follow.

EXAMPLE 1

Trifluoroacetic acid (4.30 mmol) was placed in a 30 ml stainless steel cylinder, followed by $ClSO_3F$ (4.30 mmol) after evacuation and cooling to $-196°$ C. The reactor was warmed to ambient temperature for a few hours and finally heated at 50° C. for one hour. Upon recooling to ambient temperatur the volatile products were removed under vacuum and trapped at $-196°$ C. These consisted of $CF_3Cl$ and $CO_2$, together with minor amounts of $COF_2$ and $HSO_3F$. Scrubbing with base removed the $CO_2$ and acid products furnishing $CF_3Cl$ in 90% yield.

EXAMPLE 2

Chlorodifluoroacetic acid (2.80 mmol) was loaded into a 30 ml stainless steel cylinder, followed by $ClSO_3F$ (2.91 mmol) after evacuation and cooling to $-196°$ C. After warming to ambient temperature for three hours the volatile products were separated from the relatively non-volatile $HSO_3F$ by condensation at $-196°$ C. These volatile materials consisted of $CF_2Cl_2$ and $CO_2$ mainly, plus minor amounts of $COF_2$, $SO_2F_2$, $Cl_2$, and $HSO_3F$. Scrubbing with concentrated base served to remove all the material except the $CF_2Cl_2$ which was isolated in 85% yield.

EXAMPLE 3

A 10 ml stainless steel cylinder was loaded with perfluoroglutaric acid $CF_2(CO_2H)_2$ (2.29 mmol) and, after evacuating and cooling to $-196°$ C., chlorine fluorosulfate (4.86 mmol) was condensed in and the cylinder was allowed to warm to room temperature. After several hours the volatile materials present were separated by fractional condensation in U-traps cooled to $-78°$, $-112°$, and $-196°$ C. The low temperature trap was found to contain $CO_2$ and some $SO_2F_2$. The other traps contained traces of $HSO_3F$ and $ClCF_2CF_2SO_3F$ with mainly $ClCF_2CF_2CFO$ (0.27 mmol) and $ClCF_2CF_2CF_2Cl$ (1.96 mmol). Washing with NaOH removed the acid impurities and afforded essentially pure 1.3 dichloroperfluoropropane in 86% yield. Nearly all of the low volatility by-product $HSO_3F$ was retained in the reaction cylinder.

EXAMPLE 4

Solid $CF_3CF_2CO_2Na$ (2.82 mmol) was loaded into a 10 ml stainless steel cylinder. After evacuation and cooling to $-196°$ C., $ClSO_3F$ (2.66 mmol) was condensed into the cylinder. The reactor was allowed to warm to ambient temperature overnight. Vacuum fractionation of the volatile products showed that all material passed a trap cooled to $-112°$ C. and thus all the $ClSO_3F$ had reacted. The volatile material was a mixture of $CF_3CF_2Cl$, $CO_2$ and lesser quantities of $CF_3Cl$ and $CF_3CF_2SO_3F$. The $CF_3Cl$ was attributable to reaction of impurity $CF_3CO_2Na$ in the commerical starting material. The yield of $CF_3CF_2Cl$ (2.09 mmol) was 79%.

EXAMPLE 5

Chlorine fluorosulfate (2.19 mmol) was condensed at $-196°$ C. into a 10 ml stainless steel cylinder containing $C_7F_{15}CO_2Na$ (2.26 mmol). After warming to room temperature and standing for several days the volatile products were separated by fractional condensation at $-78°$, and $-196°$ C. The low temperature condensate was a mixture of $CO_2$ and traces of an $R_fCFO$ compound, probably $C_6F_{13}CFO$. The material trapped at $-78°$ C. was $C_7F_{15}Cl$ (1.70 mmol) and $C_6F_{13}CFO$ (0.39 mmol). The yield of 1-chloroperfluoroheptane was 78%.

EXAMPLE 6

Trifluoroacetic acid (2.46 mmol) was loaded into a 30 ml stainless steel cylinder which was then cooled to $-196°$ C. and evacuated. Bromine fluorosulfate (2.31 mmol) was added to the cold cylinder and the reaction was allowed to proceed by warming the cylinder to room temperature for two hours. The products of the reaction volatile at room temperature were removed and trapped at $-196°$ C. These consisted of $CF_3Br$, $CO_2$, and minor amounts of $BR_2$, $COF_2$, and $HSO_3F$. Treatment with base removed all but the $CF_3Br$ which was obtained in 88% yield.

EXAMPLE 7

Bromine fluorosulfate (2.54 mmol) was added to a 10 ml cylinder containing $CF_3CF_2CO_2Na$ (2.76 mmol) and which was cooled to $-196°$ C. After warming first to room temperature, the cylinder was heated for 1.5 hr. at 50° C. In addition to the solid product $NaSO_3F$, the reaction furnished the volatile materials; $CO_2$, $CF_3Br$, and $CF_3CF_2Br$ (2.11 mmol). The yield of $CF_3CF_2Br$ was 83%.

While the invention has been described by reference to specific embodiments thereof, it should be understood that the instant specification and examples are presented for purposes of illustration only, and that all such modification and alterations as fall within the purview of the appended claims are intended to be included herein.

What is claimed is:

1. A method for synthesizing perfluoroalkyl halides which comprises the step of reacting:
   (a) a perfluorocarbon having the general formula $$R_fCO_2M$$

wherein $R_f$ is a saturated, straight or branched chain perfluoroalkyl radical having from one to 10 carbon atoms and M is a member of the group consisting of the alkali metals and hydrogen; and
   (b) a halogen fluorosulfate having the general formula $$XSO_3F$$

wherein X is a member selected from the group consisting of chlorine, bromine and iodine;
   (c) maintaining said reaction at an ambient temperature ranging from about 0° C. to 50° C. for a period of time sufficient to produce a perfluoroakyl halide reaction product; and
   (d) separating the resulting reaction product.

2. A method in accordance with claim 1 wherein said $R_f$ moiety is $CF_3$—, said M moiety is hydrogen, and said X moiety is chlorine.

3. A method in accordance with claim 1 wherein said $R_f$ moiety is $CF_3CF_2$—, said M moiety is sodium, and said X moiety is chlorine.

4. A method in accordance with claim 1 wherein said $R_f$ moiety is $C_7F_{15}$—, said M moiety is sodium, and said X moiety is chlorine.

5. A method in accordance with claim 1 wherein said $R_f$ moiety is $CF_3$—, said M moiety is hydrogen, and said X moiety is bromine.